United States Patent
Clement et al.

(10) Patent No.: US 7,532,197 B2
(45) Date of Patent: May 12, 2009

(54) METHOD AND SYSTEM FOR AUTOMATED MONITORING OF A DISPLAY

(75) Inventors: Thomas J. Clement, Raleigh, NC (US); Jerry W. Pearce, Apex, NC (US)

(73) Assignee: Lenovo (Singapore) Pte Ltd., Singapore (SG)

( * ) Notice: Subject to any disclaimer, the term of this patent is extended or adjusted under 35 U.S.C. 154(b) by 911 days.

(21) Appl. No.: 10/873,671

(22) Filed: Jun. 22, 2004

(65) Prior Publication Data
US 2006/0007396 A1    Jan. 12, 2006

(51) Int. Cl.
*G09G 5/00* (2006.01)
(52) U.S. Cl. .............................. 345/156; 345/7; 715/781
(58) Field of Classification Search ................. 345/156, 345/7–9; 382/103, 117; 351/205, 209; 715/700, 715/781, 802
See application file for complete search history.

(56) References Cited

U.S. PATENT DOCUMENTS

| | | | |
|---|---|---|---|
| 4,109,145 A * | 8/1978 | Graf ............................ 250/221 |
| 5,886,683 A | 3/1999 | Tognazzini et al. |
| 5,912,721 A | 6/1999 | Yamaguchi et al. |
| 6,091,334 A * | 7/2000 | Galiana et al. ............... 340/576 |
| 6,538,697 B1 * | 3/2003 | Honda et al. ............ 348/333.03 |
| 6,577,329 B1 | 6/2003 | Flickner et al. |
| 6,608,615 B1 | 8/2003 | Martins |
| 7,284,201 B2 * | 10/2007 | Cohen-Solal ................ 715/738 |
| 2003/0067476 A1 | 4/2003 | Miller et al. |
| 2003/0184561 A1 | 10/2003 | Vorst |
| 2006/0037038 A1 * | 2/2006 | Buck .............................. 725/9 |

* cited by examiner

*Primary Examiner*—Richard Hjerpe
*Assistant Examiner*—Tom V Sheng
(74) *Attorney, Agent, or Firm*—Sawyer Law Group LLP; Carlos Munoz-Bustamante

(57) ABSTRACT

Aspects for automated monitoring of a display are described. The aspects include utilizing gaze tracking with a display to monitor attention to information on the display. Additionally, a level of alarm is escalated for the updated information when the attention by the system operator is not detected within a predetermined time period.

9 Claims, 1 Drawing Sheet

METHOD AND SYSTEM FOR AUTOMATED MONITORING OF A DISPLAY

FIELD OF THE INVENTION

The present invention relates to monitoring a display, and more particularly to automated monitoring of a display.

BACKGROUND OF THE INVENTION

Computer system displays are used to present information to a system operator. In many applications, the information presented is time critical, e.g., air traffic control information. Some systems employ techniques to try and draw the operator's attention to the information, such as highlighting, blinking, color changes, etc. Typically, there is no automatic way of determining whether information on the display have been recognized by the system operator. Nor, is there any way of automatically returning a display to a normal presentation mode after the operator has recognized the information.

SUMMARY OF THE INVENTION

Aspects for automated monitoring of a display are described. The aspects include utilizing gaze tracking with a display to monitor attention to information on the display. Additionally, a level of alarm is escalated for the updated information when the attention by the system operator is not detected within a predetermined time period.

The incorporation of gaze tracking offers effective feedback in achieving the automated monitoring of the present invention. Further, with the monitoring, a seamless return to a normal presentation display occurs upon detected recognition of the information, while the provision of an alarm or other alert ensures the update is noticed upon detection of the lack of recognition. These and other advantages of the aspects of the present invention will be more fully understood in conjunction with the following detailed description and accompanying drawings.

DETAILED DESCRIPTION

The present invention relates to automated monitoring of display update recognition. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Figure 1:
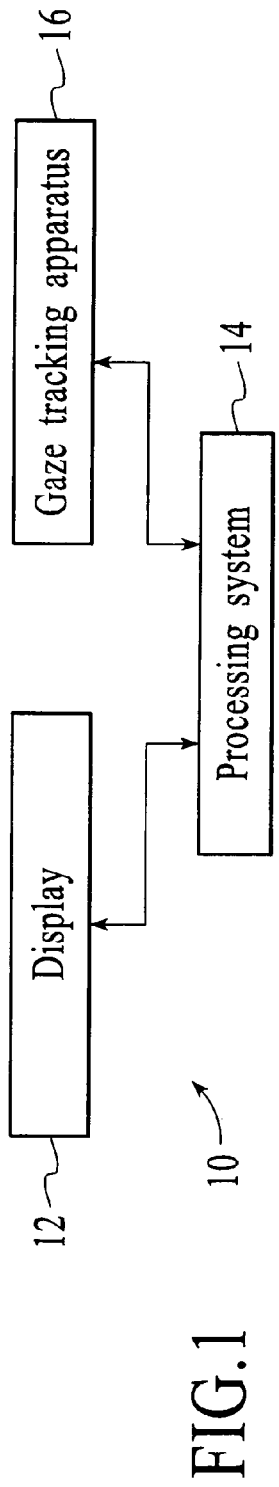
FIG. 1 illustrates a block diagram of a system for informational displays utilizing gaze tracking feedback in accordance with the present invention.

FIG. 1 illustrates a block diagram of a system 10 for informational displays utilizing gaze tracking feedback in accordance with the present invention. The system 10 includes a commercially-available display 12, for receiving data inputs such as images and the like from a processing system 14 or the like, and for providing a viewable output to a user. The display 12, operatively coupled and interfaced with the processing system 14, may be implemented by any suitable computer display with sufficient ability to depict graphical images. For example, the display 12 may include a cathode ray tube (CRT), liquid crystal display (LCD) screen, light emitting diode (LED) screen, or another suitable video apparatus. The processing system 14 may be implemented by any suitable processing system, such as a personal computer system or server system, e.g., IBM ThinkCentre Model A50P, that includes one or more central processing units (CPUs), volatile and nonvolatile memory components, storage device(s), etc., as are standard and well understood in the art.

A gaze-tracking apparatus 16 including a camera, for example, is provided either mounted in/on the display 12 or adjacent thereby and coupled to the processing system. Specifically, the gaze-tracking technology uses cameras, and infrared or other devices to sense, locate and follow the movement of a user's eyes. As described in U.S. Pat. No. 6,577,329 entitled "Method and System for Relevance Feedback through Gaze Tracking and Ticker Interfaces," a number of different gaze tracking approaches suitable for gaze tracking apparatus 16 are surveyed in Young et al., "Methods & Designs: Survey of Eye Movement Recording Methods", Behavior Research Methods & Instrumentation, 1975, Vol. 7(5), pp. 397-429. Ordinarily skilled artisans, having the benefit of this disclosure, will also recognize a number of different devices suitable for use as the apparatus 16. Also, although the invention's gaze tracking apparatus 16 may be a custom product, commercially available products may be used instead, such as the EyeTrac Series 4000 product by Applied Science Labs, or the EyeGaze system by LC Technologies, Inc., as presented in the aforementioned patent.

Commercial and research prototype eye-tracking systems locate the position of human eyes and follow their movement. Eye-tracking has been successfully used in graphic user interfaces (GUI) to assist users, such as handicapped users, in various tasks. Thus, the gaze tracking apparatus 16 monitors eye orientation of a user (operator) as the operator views a display 12 having items displayed thereon. The output from the gaze-tracking apparatus 16 (e.g., representing the movement of a user's eyes) is provided to the processing system 14. The processing system 14 in turn includes processing algorithms to map the movement of the user' eyes in terms of position on the display screen to which the user is observing, the speed of the movements of the user's eyes, and some information about the eye itself such as shape, size, etc.

In FIG. 1, the gaze tracking apparatus (e.g., camera) 16 is shown separate from the display 12. However, the camera 16 may be mounted or preferably embedded in the display 12 to detect, through the aid of the processing system 14, the user's presence, and to find/detect the location of the user's eyes. Once the location of the user's eyes is found, the direction of the user's gaze is determined by means such as described in the above mentioned patents or disclosure, incorporated herein by reference.

In accordance with the present invention, the system 10 is utilized to monitor a display automatically. The monitoring employs a gaze tracking feedback technique, which is provided on a computer readable medium in a desired programming language for performance by the processing system 14. The gaze tracking feedback is utilized to determine when/if an operator/user has looked at the display information, as described in more detail with reference to the block flow diagram representing the monitoring process in FIG. 2.

Figure 2:
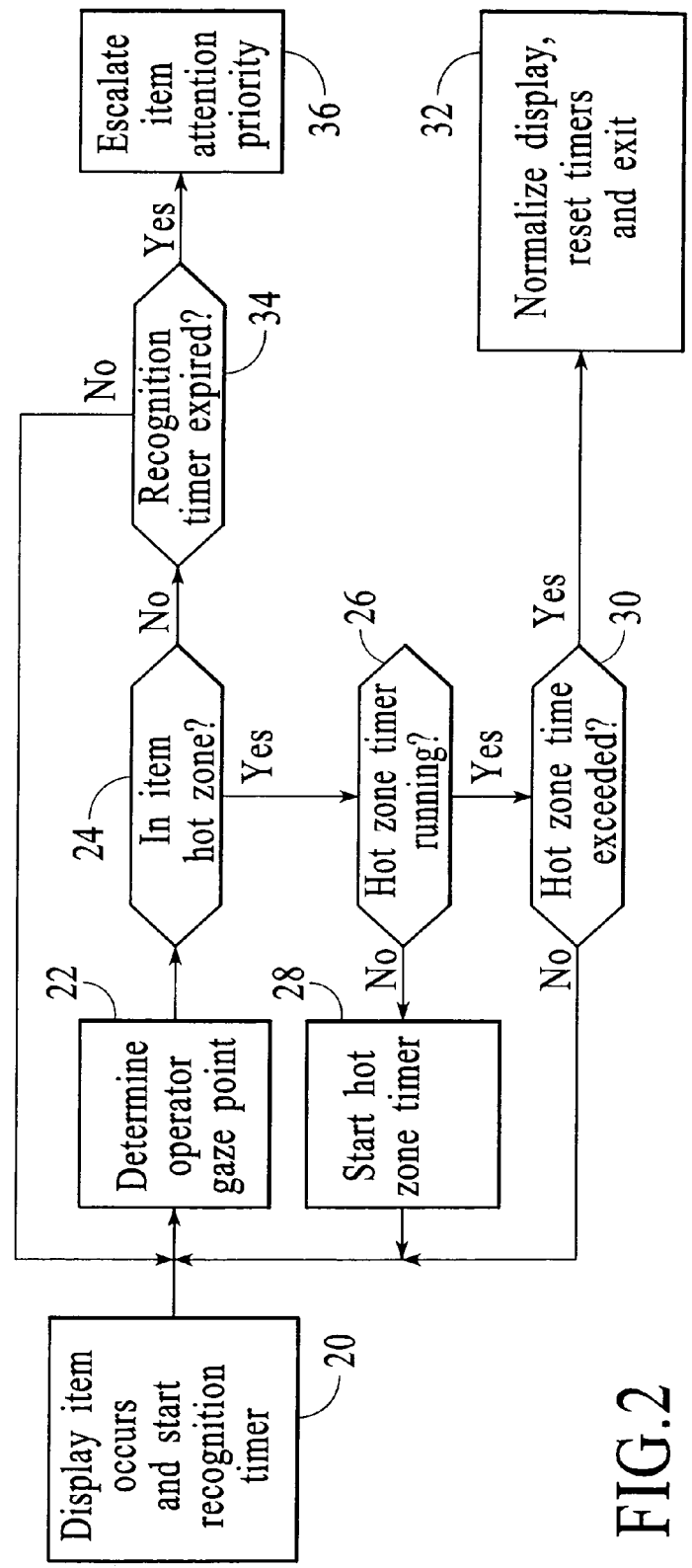
FIG. 2 illustrates a block flow diagram of a monitoring process for display update recognition in accordance with the present invention for the system of FIG. 1.

As shown in FIG. 2, the monitoring process initiates when a display items occurs, which starts a recognition timer (step 20). The recognition timer suitably provides a predetermined time period (e.g., 3 Seconds) within which recognition of the updated item is desired. Techniques such as highlighting, blinking, and/or color change may be used as a display indicator of the update. A gaze point of the operator is then determined via the data from the gaze tracking apparatus 16 (step 22). A comparison of the gaze point to a recognition area, i.e., 'hot zone', of the updated item ensues (step 24).

Once the gaze point is determined to fall within the hot zone, the length of time that the gaze point remains in the hot zone is determined. The determination occurs by first ensuring that a hot zone timer has been started (via steps 26 and 28). When the hot zone timer has already been started, but has not expired (as determined in step 30), the process continues to track the gaze point versus the hot zone. Once the gaze point remains in the hot zone for the length of time set by the hot zone timer (e.g., 2 seconds) the updated item is considered to have been recognized. Thus, the display is normalized, the timers are reset, and the process is exited (step 32).

When the gaze point is not determined to be in the hot zone (i.e., step 24 is negative), but the recognition timer has not expired (as determined via step 34), the gaze point continues to be tracked. If the gaze point does not lie within the hot zone at all or does not lie within the hot zone for the hot zone time period before the length of time set by the recognition timer expires, the updated item is not considered to have been recognized and its attention priority is escalated (step 36). For example, techniques, such as dimming the rest of the display, flashing, or an audible alarm can be used to escalate item attention priority.

Thus, with the present invention, a more automated technique of monitoring of a display occurs. The incorporation of gaze tracking offers effective feedback to achieve the monitoring. Further, the monitoring performs a seamless return to a standard display upon detected recognition of the display, while the provision of an alarm or other alert ensures the information is noticed upon detection of the lack of recognition. The automated nature of the monitoring results is greater efficiency and usability.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for automated monitoring of a display, the method comprising:
    utilizing gaze tracking to monitor attention to information on the display, the utilizing gaze tracking including determining a gaze point and comparing the gaze point to a recognition area for the information;
    escalating a level of alarm for the information in response to the attention not being detected within a predetermined time period;
    in response to the gaze point lying within the recognition area during the predetermined time period, determining whether a sufficient time period has elapsed with the gaze point within the recognition area; and
    in response to the sufficient time period having elapsed with the gaze point within the recognition area, normalizing the display of the information.

2. The method of claim 1 wherein the step of escalating occurs in response to the gaze point not lying within the recognition area during the predetermined time period.

3. The method of claim 1 wherein the step of escalating occurs in response to the a sufficient time period not having elapsed with the gaze point within the recognition area.

4. A system for automated monitoring of a display, the system comprising:
    a display;
    gaze tracking apparatus; and
    a processing system coupled to the display and the gaze tracking apparatus, the processing system utilizing gaze tracking data from the gaze tracking apparatus to monitor attention to information on the display and determining a gaze point and compares the gaze point to a recognition area for the updated information, the processing system escalating a level of alarm for the information in response to the attention not being detected within a predetermined time period,
    wherein in response to the gaze point lying within the recognition area during the predetermined time period, the processing system determines whether a sufficient time period has elapsed with the gaze point within the recognition area, and
    wherein in response to the sufficient time period having elapsed with the gaze point within the recognition area, the processing system normalizes the display of the updated information.

5. The system of claim 4 wherein in response to the gaze point not lying within the recognition area during the predetermined time period, the processing system escalates the level of alarm.

6. The system of claim 4 wherein in response to the sufficient time period not having elapsed with the gaze point within the recognition area, the processing system escalates the level of attention.

7. A computer readable medium containing program instructions for automated monitoring of a display, the program instructions comprising:
    utilizing gaze tracking to monitor attention to information on the display, the utilizing gaze tracking including determining a gaze point and comparing the gaze point to a recognition area for the information;
    escalating a level of alarm for the information in response to the attention not being detected within a predetermined time period;
    in response to the gaze point lying within the recognition area during the predetermined time period, the program instructions further comprise determining whether a sufficient time period has elapsed with the gaze point within the recognition area; and
    in response to the sufficient time period having elapsed with the gaze point within the recognition area, normalizing the display of the information.

8. The computer readable medium of claim 7 wherein the step of escalating occurs in response to the gaze point not lying within the recognition area during the predetermined time period.

9. The computer readable medium of claim 7 wherein the step of escalating occurs in response to the sufficient time period not having elapsed with the gaze point within the recognition area.

* * * * *